United States Patent
Hwang et al.

(10) Patent No.: US 10,857,044 B2
(45) Date of Patent: Dec. 8, 2020

(54) METHOD FOR PREPARING SUPERABSORBENT POLYMER

(71) Applicant: LG Chem, Ltd., Seoul (KR)

(72) Inventors: Min Ho Hwang, Daejeon (KR); Sang Gi Lee, Daejeon (KR); Hye Mi Nam, Daejeon (KR); Soo Jin Lee, Daejeon (KR); Tae Hwan Jang, Daejeon (KR)

(73) Assignee: LG Chem, Ltd. (KR)

( * ) Notice: Subject to any disclaimer, the term of this patent is extended or adjusted under 35 U.S.C. 154(b) by 209 days.

(21) Appl. No.: 15/752,783

(22) PCT Filed: Apr. 29, 2016

(86) PCT No.: PCT/KR2016/004544
§ 371 (c)(1),
(2) Date: Feb. 14, 2018

(87) PCT Pub. No.: WO2017/131291
PCT Pub. Date: Aug. 3, 2017

(65) Prior Publication Data
US 2018/0228671 A1 Aug. 16, 2018

(30) Foreign Application Priority Data
Jan. 28, 2016 (KR) .................. 10-2016-0010736

(51) Int. Cl.
| | | |
|---|---|---|
| *C08J 3/24* | (2006.01) | |
| *C08J 3/075* | (2006.01) | |
| *C08J 9/08* | (2006.01) | |
| *A61F 13/53* | (2006.01) | |
| *C08K 5/053* | (2006.01) | |
| *C08K 5/10* | (2006.01) | |
| *C08J 3/12* | (2006.01) | |
| *A61L 15/60* | (2006.01) | |
| *A61L 15/42* | (2006.01) | |
| *C08L 33/04* | (2006.01) | |

(52) U.S. Cl.
CPC .............. *A61F 13/53* (2013.01); *A61L 15/42* (2013.01); *A61L 15/60* (2013.01); *C08J 3/075* (2013.01); *C08J 3/12* (2013.01); *C08J 3/24* (2013.01); *C08J 9/08* (2013.01); *C08K 5/053* (2013.01); *C08K 5/10* (2013.01); *C08L 33/04* (2013.01); *C08J 2203/146* (2013.01); *C08J 2205/06* (2013.01); *C08J 2207/12* (2013.01)

(58) Field of Classification Search
CPC .......... A61F 13/53; A61L 15/42; A61L 15/60; C08J 3/075; C08J 3/12; C08J 3/24; C08J 9/08; C08J 2207/12; C08J 2205/06
See application file for complete search history.

(56) References Cited

U.S. PATENT DOCUMENTS

| | | | |
|---|---|---|---|
| 4,883,478 A | 11/1989 | Lerailler et al. | |
| 5,118,719 A | 6/1992 | Lind | |
| 5,314,420 A * | 5/1994 | Smith | A61F 13/15203 210/691 |
| 5,856,370 A | 1/1999 | Chmelir | |
| 5,985,944 A | 11/1999 | Ishizaki et al. | |
| 7,615,579 B2 | 11/2009 | Joy et al. | |
| 9,062,140 B2 * | 6/2015 | Fujimaru | A61L 15/60 |
| 10,086,361 B2 | 10/2018 | Won et al. | |
| 2013/0274349 A1 | 10/2013 | Qin et al. | |
| 2014/0054497 A1 | 2/2014 | Wattebled et al. | |
| 2014/0155259 A1 | 6/2014 | Tian et al. | |
| 2014/0306156 A1 | 10/2014 | Tian et al. | |
| 2014/0312273 A1 | 10/2014 | Wattebled et al. | |
| 2015/0283284 A1 * | 10/2015 | Azad | A61F 13/53 604/368 |
| 2016/0096944 A1 | 4/2016 | Wattebled et al. | |
| 2016/0184799 A1 | 6/2016 | Lee et al. | |

FOREIGN PATENT DOCUMENTS

| | | |
|---|---|---|
| CN | 104334614 A | 2/2015 |
| EP | 0538983 A1 | 4/1993 |
| EP | 0644207 A1 | 3/1995 |
| EP | 0744435 A1 | 11/1996 |
| EP | 2930191 A1 | 10/2015 |
| JP | H07185331 A | 7/1995 |
| JP | 3280077 B2 | 4/2002 |
| JP | 3852515 B2 | 11/2006 |
| KR | 20140094536 A | 7/2014 |
| KR | 101486224 B1 | 1/2015 |
| KR | 20150008055 A | 1/2015 |
| KR | 20150040476 A | 4/2015 |
| KR | 20150116418 A | 10/2015 |
| KR | 20150140800 A | 12/2015 |
| WO | 1987003208 A1 | 6/1987 |
| WO | 1996017884 A1 | 6/1996 |
| WO | 2013072268 A1 | 5/2013 |
| WO | 2014168858 A1 | 10/2014 |
| WO | 2014183987 A1 | 11/2014 |
| WO | 2015163519 A1 | 10/2015 |

OTHER PUBLICATIONS

Extended European Search Report including Written Opinion for Application No. EP16888267.8 dated Aug. 2, 2018.
Search report from International Application No. PCT/KR2016/004544, dated Sep. 12, 2016.
Schwalm, R., "UV Coatings: Basics, Recent Developments and New Applications." Elsevier Science, Dec. 21, 2006, p. 115.

(Continued)

*Primary Examiner* — Kara B Boyle
(74) *Attorney, Agent, or Firm* — Lerner, David, Littenberg, Krumholz & Mentlik, LLP

(57) ABSTRACT

The present invention relates to a method for a superabsorbent polymer. The preparation method controls the time from the addition of a foaming agent to the initiation of a polymerization reaction, thereby forming an appropriate pore structure in a superabsorbent polymer. The superabsorbent polymer produced through the preparation method can exhibit a remarkably improved absorption rate while exhibiting excellent absorption performance.

8 Claims, No Drawings

(56) References Cited

OTHER PUBLICATIONS

Odian, G.G., "Principles of Polymerization." Second Edition, John Wiley & Sons, Inc., Copyright 1981, p. 203.
Bucholz et al., "Modern Superabsorbent Polymer Technology", Wiley-VCH, 1998, pp. 69-103, Fig. 3.1.
Third Party Observation for Application No. PCT/KR2016/004544 dated May 25, 2018.
Chinese Search Report for Application No. 201680050728.2. dated Feb. 3, 2020.

* cited by examiner

METHOD FOR PREPARING SUPERABSORBENT POLYMER

CROSS-REFERENCE TO RELATED APPLICATIONS

The present application is a national phase entry under 35 U.S.C. § 371 of International Application No. PCT/KR2016/004544 filed Apr. 29, 2016, which claims priority from Korean Application No. 10-2016-0010736 filed Jan. 28, 2016, all of which are incorporated herein by reference.

BACKGROUND OF THE INVENTION (a) Field of the Invention

The present invention relates to a method for preparing a superabsorbent polymer.

(b) Description of the Related Art

A superabsorbent polymer (SAP) is a synthetic polymer material capable of absorbing moisture from about 500 to about 1000 times its own weight, and each manufacturer has called it by different names such as SAM (Super Absorbency Material), AGM (Absorbent Gel Material), or the like. Such superabsorbent polymers started to be practically applied in sanitary products, and they are now being widely used for preparation of various products, for example, hygiene products such as paper diapers for children or sanitary napkins, water retaining soil products for gardening, water stop materials for civil engineering and construction, sheets for raising seedlings, fresh-keeping agents for food distribution fields, materials for poultices, and the like.

In most cases, these superabsorbent polymers have been widely used in the field of hygienic materials such as diapers or sanitary napkin. For these applications, however, the superabsorbent polymers are required to exhibit a high moisture absorption rate. Therefore, in order to improve the absorption rate of the superabsorbent polymer, studies have continued on a technology for increasing the absorption surface area of the superabsorbent polymers.

As a method of improving the absorption rate by increasing the absorption surface area of superabsorbent polymers, a method of forming many pores inside the superabsorbent polymer to rapidly absorb water or a method of preparing the superabsorbent polymer as small particles to improve a contact surface area with water have been considered.

As the former method, a method of preparing a superabsorbent polymer by using a foaming agent, etc. was suggested, but bubbles generated by the foaming agent were not sufficiently included inside the superabsorbent polymer, and it was very difficult to control a size of the pores formed inside the superabsorbent polymer by the known method. Accordingly, the superabsorbent polymer prepared by the former method could not attain a desired level of the absorption rate.

Meanwhile, since there is a technical limitation in controlling the superabsorbent polymer to have a small particle diameter, the latter method could not sufficiently increase the absorption surface area of the superabsorbent polymer. Accordingly, there is a need for studies to increase the absorption surface area of the superabsorbent polymer.

SUMMARY OF THE INVENTION

It is one object of the present invention to provide a method for preparing a superabsorbent polymer capable of controlling the number, size, and distribution of pores formed in a superabsorbent resin by using a foaming agent.

According to an embodiment of the invention, a method for preparing a superabsorbent polymer is provided, the method including the steps of: initiating a polymerization reaction within 9 seconds from the moment when a water-soluble ethylenically unsaturated monomer having at least partially neutralized acidic groups makes contact with a foaming agent, and performing crosslinking polymerization of a monomer mixture containing a water-soluble ethylenically unsaturated monomer having at least partially neutralized acidic groups, and a foaming agent, in the presence of an internal crosslinking agent to prepare a hydrogel polymer; drying, pulverizing, and classifying the hydrogel polymer to form a base polymer powder; and additionally crosslinking the surface of the base polymer powder in the presence of a surface crosslinking agent to form a surface-crosslinked layer.

In the step of preparing the hydrogel polymer, the monomer mixture may further contain, as a foam stabilizer, an alkyl sulfate salt, an alkyl sulfonate salt, an alkyl phosphate salt, an alkyl carbonate salt, a polyethylene glycol alkyl ester, a polypropylene glycol alkyl ester, a glucoside alkyl ester, a glycerol alkyl ester, a block-copolymer of polyethylene glycol and polypropylene glycol, or a mixture thereof.

In the step of preparing the hydrogel polymer, a foaming agent may be added to the monomer mixture. Specifically, in the step of preparing the hydrogel polymer, the foaming agent may be added to the monomer mixture in a solid or liquid state without dilution, the foaming agent may added in a solution state after being diluted in a solvent, the foaming agent may be added by spraying, or the forming agent may be added by spraying it on a coating film obtained by coating the monomer mixture.

As the foaming agent, an inorganic foaming agent may be used. As the inorganic forming agent, at least one carbonate selected from the group consisting of sodium hydrogen carbonate, sodium carbonate, potassium hydrogen carbonate, and potassium carbonate may be used. The foaming agent may be used in an amount of 0.001 to 1% by weight based on the total amount of the monomer mixture.

In the step of preparing the hydrogel polymer, the polymerization reaction may be initiated within 5 seconds from the moment when a water-soluble ethylenically unsaturated monomer having at least partially neutralized acidic groups makes contact with a foaming agent. Thereby, a crosslinked polymer having an appropriate pore structure formed therein can be produced.

Meanwhile, as the internal crosslinking agent, at least one selected from the group consisting of polyethylene glycol diacrylate, glycerin diacrylate, glycerin triacrylate, unmodified or ethoxylated trimethylolpropane triacrylate, hexanediol diacrylate, and triethylene glycol diacrylate may be used. As the surface crosslinking agent, at least one polyol selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, and glycerol, or at least one carbonate compound selected from the group consisting of ethylene carbonate and propylene carbonate, may be used.

The superabsorbent polymer produced through the preparation method according to this embodiment can exhibit features that it has a centrifuge retention capacity (CRC) for a physiological saline solution of 29 to 33 g/g and absorbency under load (AUL) of under 0.9 psi for a physiological saline solution of 14 to 22 g/g, and a vortex time of 20 to 40 seconds.

The preparation method according to one embodiment of the present invention can control the time from the addition of a foaming agent to the initiation of a polymerization reaction, thereby forming an appropriate pore structure in a superabsorbent polymer. The superabsorbent polymer produced through the preparation method can exhibit a remarkably improved absorption rate while exhibiting excellent absorption performance.

DETAILED DESCRIPTION OF THE EMBODIMENTS

Hereinafter, a method for preparing a superabsorbent polymer according to a specific embodiment of the present invention will be described.

According to one embodiment of the invention, a method for preparing a superabsorbent polymer is provided, the method including the steps of: initiating a polymerization reaction within 9 seconds from the moment when a water-soluble ethylenically unsaturated monomer having at least partially neutralized acidic groups makes contact with a foaming agent, and performing crosslinking polymerization of a monomer mixture containing a water-soluble ethylenically unsaturated monomer having at least partially neutralized acidic groups, and a foaming agent in the presence of an internal crosslinking agent to prepare a hydrogel polymer; drying, pulverizing, and classifying the hydrogel polymer to form a base polymer powder; and additionally crosslinking the surface of the base polymer powder in the presence of a surface crosslinking agent to form a surface-crosslinked layer.

In the technical field to which the present invention belongs, a technique of using a foaming agent for improving the absorption rate of a superabsorbent polymer is known. However, these foaming agents have a limit in forming sufficient pores in the superabsorbent polymer by being decomposed by a neutralizing agent or the like used for the neutralization of monomers. Therefore, the present inventors conducted extensive studies and found that the time from the addition of a foaming agent to the monomer mixture to the initiation of a polymerization reaction exerts a large influence on the foaming efficiency, and by adjusting this time, the superabsorbent resin can control the number, size, and distribution of pores, and the like.

Specifically, in the preparation method according to one embodiment, the polymerization reaction is initiated within 9 seconds from the moment when the water-soluble ethylenically unsaturated monomer having at least partially neutralized acidic groups makes contact with the foaming agent to thereby produce a hydrogel polymer. Therefore, it is possible to provide a superabsorbent polymer exhibiting a remarkably improved absorption rate while exhibiting excellent centrifuge retention capacity and absorbency under load.

The method for preparing a superabsorbent polymer according to one embodiment will be described in more detail below.

In the step of preparing the hydrogel polymer, first, raw materials excluding the foaming agent are mixed to prepare a monomer mixture. Such raw materials may include, but are not limited to, a water-soluble ethylenically unsaturated monomer, a neutralizing agent, an internal crosslinking agent, a polymerization initiator, and the like.

The water-soluble ethylenically unsaturated monomer may include at least one selected from the group consisting of anionic monomers of (meth)acrylic acid, maleic acid, maleic anhydride, fumaric acid, crotonic acid, itaconic acid, sorbic acid, vinylphosphonic acid, vinylsulfonic acid, allylsulfonic acid, 2-(meth)acryloylethanesulfonic acid, 2-(meth)acryloyloxyethanesulfonic acid, 2-(meth)acryloylpropanesulfonic acid or 2-(meth)acrylamido-2-methylpropanesulfonic acid, and their salts; non-ionic hydrophilic group-containing monomers of (meth)acrylamide, N-substituted (meth)acrylamide, 2-hydroxyethyl(meth)acrylate, 2-hydroxypropyl(meth)acrylate, methoxypolyethylene glycol(meth)acrylate, or polyethylene glycol (meth)acrylate; and amino group-containing unsaturated monomers of (N,N)-dimethylaminoethyl (meth)acrylate or (N,N)-dimethylaminopropyl (meth)acrylamide, and their quaternary products.

In particular, the water-soluble ethylenically unsaturated monomer may be composed of a monomer (a salt of an anionic monomer) in which at least a part of an acidic group included in the anionic monomer is neutralized.

More specifically, as the water-soluble ethylenically unsaturated monomer, acrylic acid or a salt thereof may be used, and when acrylic acid is used, at least a part thereof may be neutralized and used. The use of such monomers makes it possible to produce a superabsorbent polymer having excellent physical properties. For example, when an alkali metal salt of acrylic acid is used as the water-soluble ethylenically unsaturated monomer, acrylic acid may be used by neutralizing it with a neutralizing agent such as sodium hydroxide (NaOH). At this time, the neutralization degree of the acrylic acid can be adjusted to about 50 to 95 mol % or about 60 to 85 mol %, and within this range, a superabsorbent polymer having excellent retention capacity without fear of precipitation during neutralization can be provided.

In the monomer mixture containing the water-soluble ethylenically unsaturated monomer, the concentration of the water-soluble ethylenically unsaturated monomer may be about 20% to about 60% by weight, or about 25% to about 50% by weight, based on the total amount of the monomer mixture including respective raw materials described below, a foaming agent, an additive, and a solvent, which may be appropriately adjusted in consideration of polymerization time, reaction conditions, and the like. However, if the concentration of the monomer is excessively low, the yield of the superabsorbent polymer can be lowered and thus economic problems may arise. On the other hand, if the concentration is excessively high, it may give rise to problems in the processes, for example, a part of the monomer may be precipitated, the pulverization efficiency may be lowered during pulverization of the polymerized hydrogel polymer, etc., and the physical properties of the superabsorbent polymer may be deteriorated.

The internal crosslinking agent is included in the monomer mixture to crosslink the water-soluble ethylenically unsaturated monomer. The internal crosslinking agent is composed of a compound containing two or more crosslinkable functional groups in the molecule. The internal crosslinking agent may include a carbon-carbon double bond in the crosslinkable functional group for smooth crosslinking polymerization reaction of the water-soluble ethylenically unsaturated monomer. More specific examples of these internal crosslinking agents include at least one selected from the group consisting of polyethylene glycol diacrylate (PEGDA), glycerine diacrylate, glycerin triacrylate, unmodified or ethoxylated trimethylolpropane triacrylate (TMPTA), hexanediol diacrylate, and triethylene glycol diacrylate.

The internal crosslinking agent can be contained at a concentration of about 0.01 to about 2% by weight based on the monomer mixture, thereby forming a cross-linked polymer exhibiting a high absorption rate while having excellent absorption capacity and absorbency under load.

As the polymerization initiator, a polymerization initiator generally used in the technical field to which the present invention pertains can be used.

Specifically, the polymerization initiator can be appropriately selected depending on the polymerization method. When a thermal polymerization method is used, a thermal polymerization initiator is used. When a photo-polymerization method is used, a photo-polymerization initiator is used. When a hybrid polymerization method (a method using both thermal and photo) is used, both a thermal polymerization initiator and a photo-polymerization initiator can be used. However, even in the case of the photo-polymerization method, a certain amount of heat is generated by light irradiation such as ultraviolet irradiation or the like, and a certain amount of heat is generated in accordance with the progress of the polymerization reaction, which is an exothermic reaction, and thus a thermal polymerization initiator may be further included.

The photo-polymerization initiator can be used without particular limitation as long as it is a compound capable of forming a radical by light such as ultraviolet rays.

The photo-polymerization initiator used herein may include, for example, one or more compounds selected from the group consisting of benzoin ether, dialkyl acetophenone, hydroxyl alkylketone, phenyl glyoxylate, benzyl dimethyl ketal, acyl phosphine, and α-aminoketone. Meanwhile, specific examples of the acylphosphine include diphenyl(2,4,6-trimethylbenzoyl)phosphine oxide, phenylbis(2,4,6-trimethylbenzoyl)phosphine oxide, ethyl(2,4,6-trimethylbenzoyl)phenylphosphinate, and the like. More various photo-polymerization initiators are well disclosed in "UV Coatings: Basics, Recent Developments and New Application" written by Reinhold Schwalm, (Elsevier, 2007), p. 115, the content of which is incorporated herein by reference.

The photo-polymerization initiator may be added in a concentration of about 0.0001 to 1% by weight based on the monomer composition. When the concentration of the photo-polymerization initiator is too low, the polymerization rate may become slow, and when the concentration of the photo-polymerization initiator is too high, the molecular weight of the superabsorbent polymer may be small and the physical properties may become uneven.

Further, as the thermal polymerization initiator, at least one selected from the group consisting of a persulfate-based initiator, an azo-based initiator, hydrogen peroxide, and ascorbic acid can be used. Specifically, examples of the persulfate-based initiators include sodium persulfate ($Na_2S_2O_8$), potassium persulfate ($K_2S_2O_8$), ammonium persulfate (($NH_4)_2S_2O_8$), and the like, and examples of the azo-based initiator include 2,2-azobis(2-amidinopropane) dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, 4,4-azobis-(4-cyanovaleric acid), and the like. More various thermal polymerization initiators are well disclosed in "Principle of Polymerization" written by Odian, (Wiley, 1981), p. 203, the content of which is incorporated herein by reference.

The thermal polymerization initiator may be included at a concentration of about 0.001 to about 1.0% by weight based on the monomer mixture. If the concentration of such a thermal polymerization initiator is too low, additional thermal polymerization hardly occurs and the effect due to the addition of the thermal polymerization initiator may be insignificant. If the concentration of the thermal polymerization initiator is excessively high, the molecular weight of the superabsorbent polymer may be small and the physical properties may become uneven.

In addition, the monomer mixture may further include additives such as a foam stabilizer, a thickener, a plasticizer, a preservation stabilizer, an antioxidant, and the like, if necessary.

Among them, as the foam stabilizer, an alkyl sulfate salt, an alkyl sulfonate salt, an alkyl phosphate salt, an alkyl carbonate salt, a polyethylene glycol alkyl ester, a polypropylene glycol alkyl ester, a glucoside alkyl ester, a glycerol alkyl ester, a block-copolymer of polyethylene glycol and polypropylene glycol, or a mixture thereof can be used.

In this case, the alkyl group is not particularly limited, and may be a linear, branched, or cyclic alkyl group having 1 to 30 carbon atoms or the like. This foam stabilizer is contained at a concentration of about 0.0001 to 0.1% by weight, or about 0.001 to 0.1% by weight based on the monomer mixture, to improve the foaming efficiency of the foaming agent, thereby forming a crosslinked polymer having an appropriate pore structure.

The raw materials such as the above-mentioned water-soluble ethylenically unsaturated monomers, neutralizing agents, internal crosslinking agents, polymerization initiators, and additives can be prepared in a form dissolved in a solvent.

In this case, any usable solvent can be used without limitation in the constitution as long as it can dissolve the above-mentioned raw material. Examples of the solvent may include at least one selected from the group consisting of water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, and the like.

The solvent may be contained in a residual amount excluding the above-mentioned components with respect to the total content of the monomer mixture.

In the step of preparing the hydrogel polymer, a monomer mixture may be prepared by mixing raw materials such as the above-mentioned water-soluble ethylenically unsaturated monomers, neutralizing agents, internal cross-linking agents, polymerization initiators, and additives. At this time, the order of mixing the raw materials is not particularly limited.

After mixing the above raw materials to prepare a monomer mixture, a foaming agent may be added to the monomer mixture before the monomer mixture is polymerized. The method of adding the foaming agent is not particularly limited. As a non-limiting example, the foaming agent may be added to the monomer mixture in a solid or liquid state without dilution, the foaming agent may be added in a solution state after being diluted in a solvent, the foaming agent may be added by spraying it onto the monomer mixture, or the forming agent may be added by spraying it on the coating film obtained by coating the monomer mixture.

An inorganic foaming agent may be used as the foaming agent in the preparation method according to one embodiment. Specifically, as the inorganic foaming agent, at least one carbonate selected from the group consisting of sodium bicarbonate, sodium carbonate, potassium bicarbonate, and potassium carbonate may be used.

The foaming agent may be used in an amount of 0.001 to 1% by weight or 0.05 to 1% by weight based on the total amount of the monomer mixture, and within these ranges, a crosslinked polymer having a proper pore structure formed therein may be provided.

In the step of preparing the hydrogel polymer, the polymerization reaction may be initiated within 9 seconds from the moment when a water-soluble ethylenically unsaturated monomer having at least partially neutralized acidic groups makes contact with a foaming agent by adding a foaming agent to the monomer mixture.

In the present specification, the time from the moment when a water-soluble ethylenically unsaturated monomer having at least partially neutralized acidic groups makes contact with a foaming agent to the time point of initiation of the polymerization reaction is referred to as 'mixing time of foaming agent'.

If the mixing time of the foaming agent is 10 seconds or more, the foaming agent may be decomposed by a neutralizing agent used for neutralizing the water-soluble ethylenically unsaturated monomer, a water-soluble ethylenically unsaturated monomer having an acidic group neutralized by the neutralizing agent, a by-product produced by the neutralizing agent, or other components in the monomer mixture, and a part of the foaming agent may be foamed before the polymerization is initiated. Consequently, it is difficult to obtain a crosslinked polymer having the desired pore structure because sufficient foaming does not occur in the polymerization step, or the pore size becomes too large due to aggregation of bubbles generated before the polymerization step. However, when the mixing time of the foaming agent is within 9 seconds, within 8 seconds, within 7 seconds, within 6 seconds, or within 5 seconds, decomposition of the foaming agent can be suppressed and thus the foaming efficiency can be improved, such that it is possible to obtain a crosslinked polymer in which pores of an appropriate size are sufficiently formed. In particular, when the mixing time of the foaming agent is within 5 seconds, a superabsorbent polymer exhibiting a more improved absorption rate can be provided. In the step of preparing the hydrogel polymer, since the polymerization reaction can be initiated simultaneously when the foaming agent is added to the monomer mixture, the mixing time of the foaming agent may be 0 seconds.

In the step of preparing the hydrogel polymer, the monomer mixture can be polymerized by various methods known in the technical field to which the present invention belongs. As a non-limiting example, the monomer mixture may be thermally polymerized or photo-polymerized, or may be hybrid-polymerized by heat and light. When the monomer mixture is thermally polymerized, the time point of initiation of the polymerization reaction is the time when heat is applied to the monomer mixture, or the time when the monomer mixture is added to a heated reactor. When the monomer mixture is photo-polymerized, the time point of initiation of the polymerization reaction can be the time point of initiation of the light irradiation. When the monomer mixture is hybrid-polymerized by heat and light, the time point of initiation of the polymerization reaction is the time point of initiation of the polymerization reaction in the polymerization method which proceeds in advance.

In the case of thermal polymerization, usually, it may be carried out in a reactor like a kneader equipped with agitating spindles. In the case of the photo-polymerization, it may be carried out in a reactor equipped with a movable conveyor belt. However, the above-described polymerization method is only an example, and the present invention is not limited thereto.

For example, the monomer mixture may be thermally polymerized by providing hot air to a reactor like a kneader equipped with the agitating spindles, or heating the reactor. The hydrogel polymer thus obtained from the thermal polymerization as described above is discharged from the outlet of the reactor, and may have a size of several centimeters or several millimeters according to the type of agitating spindles equipped in the reactor. Specifically, the size of the hydrogel polymer may vary depending on the concentration of the monomer mixture to be injected thereto, the injection speed, or the like, and the hydrogel polymer having an average particle diameter of about 2 to 50 mm may be generally obtained.

Further, as described above, when the photo-polymerization is carried out in a reactor equipped with a movable conveyor belt, the hydrogel polymer may be obtained in a sheet-type having a width of the belt. The thickness of the polymer sheet may vary depending on the concentration of the monomer mixture to be injected thereto, the injection speed, and the degree of foaming of the foaming agent. The monomer mixture may be coated onto the conveyor belt such that the thickness of the coating film before polymerization is about 0.5 to 5 cm. In such a range, the polymerization reaction can be uniformly carried out over the entire thickness and high production efficiency can be exhibited. However, the coating amount of the monomer mixture is not limited to the above range.

The light source usable in the photo-polymerization method is not particularly limited, and as a non-limiting example, a light source such as a Xe lamp, a mercury lamp, or a metal halide lamp can be used.

The hydrogel polymer formed by the above-mentioned method may have a water content of about 40 to about 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the drying process by raising the temperature of the polymer through infrared heating. At this time, the water content is measured under the drying conditions determined as follows: the drying temperature is increased from room temperature to about 180° C. and then the temperature may be maintained at 180° C., and the total drying time may be set to 20 minutes, including 5 minutes for the temperature rising step.

After the monomers are polymerized into cross-linked polymer, the base polymer powder can be obtained through steps of drying, pulverization, classification, and the like, and through these steps, the base polymer powder and the superabsorbent polymer obtained therefrom are suitably produced and provided so as to have a particle diameter of about 150 to 850 μm. More specifically, at least about 95% by weight or more of the base polymer powder and the superabsorbent polymer obtained therefrom has a particle diameter of about 150 μm to 850 μm, and the fine powder having a particle diameter of less than about 150 μm can contain less than about 3% by weight.

As the particle diameter distribution of the base polymer powder and the superabsorbent polymer is adjusted to the preferable range, the superabsorbent polymer finally produced can exhibit excellent centrifuge retention capacity and absorbency under load.

Meanwhile, the method of drying, pulverization, and classification will be described in more detail.

First, in the drying of the hydrogel polymer, a step of coarse pulverization may be further carried out before drying to improve the efficiency of the drying step, if necessary.

A pulverizing machine used herein may include, for example, any one selected from the group consisting of a vertical pulverizing device, a turbo cutter, a turbo grinder, a rotary cutter mill, a cutter mill, a disc mill, a shred crusher, a crusher, a chopper, and a disc cutter. However, it is not limited to the above-described examples.

In this case, the coarsely pulverizing step may be carried out so that the particle diameter of the hydrogel polymer becomes about 0.1 to about 10 mm.

Pulverizing the hydrogel polymer into a particle diameter of less than 0.1 mm is technically not easy due to its high water content, and agglomeration may occur between the pulverized particles. Meanwhile, if the polymer is pulverized into a particle diameter of greater than 10 mm, the effect of increasing the efficiency in the subsequent drying step may be insignificant.

The hydrogel polymer coarsely pulverized as described above or the hydrogel polymer immediately after polymerization without the coarsely pulverizing step is subjected to a drying step. In this case, the drying temperature of the drying step may be about 150° C. to about 250° C. When the drying temperature is less than 150° C., it is likely that the drying time would become too long and it is likely that the physical properties of the superabsorbent polymer finally formed would be deteriorated, and when the drying temperature is higher than 250° C., only the surface of the polymer is excessively dried, and thus it is likely that fine powder may be generated during the subsequent pulverizing step and the physical properties of the superabsorbent polymer finally formed would be deteriorated. Therefore, the drying may be preferably carried out at a temperature of about 150° C. to about 200° C., more preferably 160° C. to about 180° C.

Meanwhile, the drying time may be about 20 minutes to about 90 minutes, in consideration of the process efficiency and the like, but it is not limited thereto.

The drying method may also be selected and used without limitation in the constitution if it is a method generally used for drying the hydrogel polymer. Specifically, the drying step may be carried out by a method such as hot air supply, infrared irradiation, microwave irradiation, or ultraviolet irradiation. The water content of the polymer after such a drying step may be about 0.1% to about 10% by weight.

Next, a step of pulverizing the dried polymer obtained through such a drying step is carried out.

The polymer powder obtained after the pulverizing step may have a particle diameter of about 150 μm to about 850 μm. Specific examples of a pulverizing device that can be used for pulverizing the polymer to have the above particle size may include a pin mill, a hammer mill, a screw mill, a roll mill, a disc mill, a jog mill, or the like, but it is not limited thereto.

Also, in order to control the physical properties of the superabsorbent polymer powder finally commercialized after the pulverization step, a separate step of classifying the polymer powder obtained after the pulverization depending on the particle diameter may be undertaken. Preferably, a polymer having a particle diameter of about 150 to about 850 μm is classified, and only the polymer powder having such a particle diameter is subjected to the surface crosslinking reaction and finally commercialized. Since the particle diameter distribution of the base polymer powder obtained through such a process has already been described above, a further detailed description thereof will be omitted.

Meanwhile, after the step of forming the base polymer powder described above, the surface crosslinked layer can be formed by additionally crosslinking the surface of the base polymer powder in the presence of the surface crosslinking agent, whereby the superabsorbent resin can be produced.

As the surface crosslinking agent, any surface crosslinking agent conventionally used in the production of a superabsorbent polymer can be used without particular limitation. More specific examples of the surface crosslinking agent include polyols such as ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, and glycerol; or carbonate compounds such as ethylene carbonate and propylene carbonate. Such a surface cross-linking agent may be used in an amount of about 0.01 to 3% by weight based on the total weight of the base polymer powder.

Further, in the surface cross-linking step, in addition to the above-mentioned surface crosslinking agent, at least one inorganic filler selected from the group consisting of silica, clay, alumina, a silica-alumina composite, titania, zinc oxide, and aluminum sulfate is added to carry out the surface crosslinking reaction.

The inorganic material may be used in the form of powder or liquid, and in particular, it can be used as alumina powder, silica-alumina powder, titania powder, or a nanosilica solution. In addition, the inorganic material may be used in an amount of about 0.05 to about 2% by weight based on the total weight of the base polymer powder.

Furthermore, in the surface crosslinking step, the surface crosslinking structure of the superabsorbent polymer can be further optimized as the surface crosslinking proceeds by adding a multivalent metal cation in place of or in addition to the inorganic material. This is presumably because these metal cations can further reduce the crosslinking distance by forming a chelate with the carboxyl group (COOH) of the superabsorbent polymer.

The method of adding the surface crosslinking agent and optionally the inorganic material and/or the polyvalent metal cation to the base polymer powder is not particularly limited. For example, a method of adding a surface crosslinking agent and a base polymer powder to a reaction tank and mixing them, a method of spraying a surface crosslinking agent or the like onto the base polymer powder, a method of continuously providing a base polymer powder and a surface crosslinking agent to a continuously operated mixer, or the like, can be used.

When the surface crosslinking agent is added, water and methanol can be additionally mixed and added. When water and methanol are added, there is an advantage that the surface crosslinking agent can be uniformly dispersed in the base polymer powder. At this time, the content of water and methanol to be added can be appropriately adjusted for the purpose of inducing uniform dispersion of the surface cross-linking agent, preventing the aggregation phenomenon of the base polymer powder, and optimizing the penetration depth of the surface of the crosslinking agent.

The surface crosslinking reaction can be carried out by heating the base polymer powder to which the surface crosslinking agent is added at about 100° C. or more for about 20 minutes or longer. In particular, in order to produce a superabsorbent polymer which can more effectively exhibit the above-mentioned effects, the conditions of the surface cross-linking step can be adjusted so that the maximum reaction temperature is about 100 to 250° C.

Then, the retention time at the maximum reaction temperature can be adjusted to conditions of about 20 minutes or more, or about 20 minutes to 1 hour or less. In addition, the temperature raising time required to reach from a temperature at the start of the first reaction, for example, a temperature of about 100° C. or more, to the maximum reaction temperature can be controlled to about 10 minutes or more, or about 10 minutes or more and 1 hour or less.

The temperature raising means for the surface crosslinking reaction is not particularly limited. The heating can be carried out by providing a heating medium or directly providing a heating source. The type of heat medium that can be used here includes a heated fluid such as steam, hot air, hot oil, etc., but it is not limited to thereto. Further, the temperature of the heating medium to be provided can be appropriately selected in consideration of the means of the heating medium, the temperature raising speed, and the temperature raising target temperature. Meanwhile, as a heat source to be provided directly, a heating method using electricity or a heating method using gas may be mentioned, but is not limited to the above example.

The superabsorbent polymer obtained according to the preparation method of one embodiment described above exhibits excellent physical properties such as a centrifuge retention capacity and absorbency under load, and can exhibit a particularly high absorption rate.

More specifically, the superabsorbent polymer prepared according to the preparation method of this embodiment may exhibit features that it has a centrifuge retention capacity (CRC) for a physiological saline solution of 29 to 33 g/g and absorbency under load (AUL) of under 0.9 psi for a physiological saline solution of 14 to 22 g/g, and a vortex time of 20 to 40 seconds.

The centrifuge retention capacity (CRC) for a physiological saline solution can be measured according to an EDANA recommended test method No. WSP 241.2. More specifically, the centrifuge retention capacity can be calculated according to the following Calculation Equation 1 after absorbing the superabsorbent polymer in a physiological saline solution for 30 minutes.

$$CRC(g/g) = \{[W_2(g) - W_1(g)]/W_0(g)\} - 1 \quad \text{[Calculation Equation 1]}$$

In the above Calculation Equation 1, $W_0(g)$ is an initial weight (g) of the superabsorbent polymer, $W_1(g)$ is a weight of an empty bag not including the superabsorbent polymer, which is measured after dehydrating the superabsorbent polymer by using a centrifuge at 250 G for 3 minutes, and $W_2(g)$ is a weight of the bag including the superabsorbent polymer, which is measured after immersing and absorbing the superabsorbent polymer in a physiological saline solution (0.9 wt % sodium chloride aqueous solution) at room temperature for 30 minutes and then dehydrating the same by using a centrifuge at 250 G for 3 minutes.

Further, the absorbency under load (AUL) of under 0.9 psi can be measured according to an EDANA recommended test method No. WSP 242.2. More specifically, the absorbency under load can be calculated according to the following Calculation Equation 2 after absorbing the superabsorbent polymer in a physiological saline solution under a load of about 0.9 psi for 1 hour, $$AUL(g/g) = [W_4(g) - W_3(g)]/W_0(g) \quad \text{[Calculation Equation 2]}$$

in the above Calculation Equation 2, $W_0(g)$ is an initial weight (g) of the superabsorbent polymer, $W_3(g)$ is the total sum of a weight of the superabsorbent polymer and a weight of the device capable of providing a load to the superabsorbent polymer, $W_4(g)$ is the total sum of a weight of the superabsorbent polymer and a weight of the device capable of providing a load to the superabsorbent polymer, after absorbing a physiological saline solution in the superabsorbent polymer under a load (about 0.9 psi) for 1 hour.

$W_0(g)$ described in the above-mentioned Calculation Equations 1 and 2 corresponds to the initial weight (g) before absorbing the superabsorbent polymer in a physiological saline solution, and each may be the same or different.

The vortex time can be measured in seconds according to the method described in International Publication WO 1987/003208. More specifically, the vortex time (or absorption rate) was calculated by measuring in seconds the amount of time required for the vortex to disappear after adding 2 grams of a superabsorbent polymer to 50 mL of physiological saline solution and then stirring the mixture at 600 rpm. The vortex time of the superabsorbent polymer may be the absorption rate which is measured by using a superabsorbent polymer having a particle diameter of 90 to 850 μm which was passed through a U.S. standard 20 mesh screen and retained on a U.S. standard 170 mesh screen.

Through the physical properties as described above, the superabsorbent polymer produced by the preparation method of one embodiment not only has excellent basic absorption properties but can also exhibit a remarkably improved absorption rate. Thus, it is expected that the superabsorbent polymer can be applied to various sanitary articles such as diapers, to exhibit excellent physical properties as a whole.

Hereinafter, the action and effects of the present invention will be described in detail by way of specific examples. However, these examples are given for illustrative purposes only, and the scope of the invention is not intended to be limited thereto.

Example 1: Preparation of Superabsorbent Polymer

To the glass reactor, 500 g of acrylic acid, 1.02 g of polyethylene glycol diacrylate (molecular weight 400 g/mol) as an internal crosslinking agent, 0.68 g of trimethylolpropane triacrylate containing 9 mol % of ethylene oxide (ethoxylated-TMPTA, TMP (EO) 9TA, M-3190 manufactured by Miwon Specialty Chemical Co., Ltd.), and 0.04 g of IRGACURE 819 as a photopolymerization initiator were added. Then, 24 wt % of a caustic soda solution (NaOH aqueous solution) was slowly added dropwise so that about 75 mol % of acrylic acid was neutralized with respect to the total amount of the acrylic acid. The temperature of the monomer mixture was increased to about 72° C. or higher due to neutralization heat during the dropwise addition of the caustic soda solution. After cooling the monomer mixture, 1.02 g of sodium bicarbonate as a foaming agent was injected in the form of a 4 wt % aqueous solution. Then, the monomer mixture prepared above was poured in a Vat-type tray (15 cm in width×15 cm in length) installed in a square polymerizer which had a light irradiation device installed at the top and was preheated to 80° C. Subsequently, the monomer mixture was irradiated with light. That is, the contact between the neutralized acrylic acid and the foaming agent, and the light irradiation, were performed almost simultaneously. It was confirmed that a gel was formed on the surface after about 20 seconds from light irradiation, and it was confirmed that the polymerization reaction occurred simultaneously with foaming after about 25 seconds from light irradiation. Subsequently, the reaction was allowed to continue for an additional 2 minutes, and the polymerized sheet was taken out and cut into a size of 5 cm×5 cm. Then, the cut sheet was subjected to a chopping process using a meat chopper to prepare crumbs.

The crumbs were then dried in an oven capable of shifting airflow upward and downward. The crumbs were uniformly dried by flowing hot air at 180° C. from the bottom to the top for 15 minutes and again from the top to the bottom for 15 minutes, and thereby a water content of the dried product was set to 2% or less. The dried product was pulverized using a pulverizer and classified into a size of 150 to 850 μm to obtain a base polymer.

Thereafter, 100 g of the base polymer was mixed with a crosslinking agent solution obtained by mixing 3 g of water, 3.5 g of methanol, 0.4 g of ethylene carbonate, and 0.1 g of Aerosil 380 (EVONIK), and then a surface crosslinking reaction was carried out at 190° C. for 50 minutes. The resultant was pulverized and sieved to obtain a surface-crosslinked superabsorbent polymer having a particle diameter of 90 to 850 μm.

Example 2: Preparation of Superabsorbent Polymer

A superabsorbent polymer was prepared in the same manner as in Example 1, except that 0.025 g of S1670 (Ryoto Sugar Ester S-1670, manufactured by Mitsubishi Chemical Food Corporation) as a foam stabilizer was further added to the monomer mixture before adding the foaming agent in Example 1.

Example 3: Preparation of Superabsorbent Polymer

A superabsorbent polymer was prepared in the same manner as in Example 2, except that the time between the contact of the neutralized acrylic acid with the foaming agent and the light irradiation was adjusted to about 5 seconds, by adding the foaming stabilizer to the monomer mixture before adding the foaming agent as in Example 2, and then adding the foaming agent thereto, mixing the monomer mixture for about 5 seconds, pouring the mixture in a tray used in Example 1, and irradiating light.

Example 4: Preparation of Superabsorbent Polymer

The monomer mixture excluding the foaming agent in Example 2 was added to the slope surface of the tray used in Example 2, and the foaming agent solution (containing 1.02 g of sodium bicarbonate with a 4 wt % sodium hydrogen carbonate aqueous solution) was sprayed onto the monomer mixture flowing on the slope surface. The time required for the injection of the monomer mixture and the spraying of the foaming agent solution was adjusted to about 5 seconds. A superabsorbent polymer was obtained in the same manner as in Example 2, except that the time between the contact of the neutralized acrylic acid with the foaming agent, and the light irradiation, was adjusted to about 5 seconds by irradiation of light after the injection of the monomer mixture and the spraying of the foaming agent solution were completed.

Comparative Example 1: Preparation of Superabsorbent Polymer

A superabsorbent polymer was obtained in the same manner as in Example 2, except that the time between the contact of the neutralized acrylic acid with the foaming agent, and the light irradiation, was adjusted to about 20 seconds by mixing the monomer mixture for about 20 seconds after the addition of the foaming agent in Example 1, pouring the mixture in the tray used in Example 1, and irradiating light.

Comparative Example 2: Preparation of Superabsorbent Polymer

A superabsorbent polymer was obtained in the same manner as in Example 1, except that the time between the contact of the neutralized acrylic acid and the foaming agent, and the light irradiation, was adjusted to about 60 seconds by mixing the monomer mixture for about 60 seconds after the addition of the foaming agent in Example 1, pouring the mixture in the tray used in Example 1, and irradiating light.

Comparative Example 3: Preparation of Superabsorbent Polymer

A superabsorbent polymer was obtained in the same manner as in Example 2, except that the time between the contact of the neutralized acrylic acid with the foaming agent, and the light irradiation, was adjusted to about 10 seconds by adding the foaming stabilizer to the monomer mixture before adding the foaming agent as in Example 2, and then adding the foaming agent thereto, mixing the monomer mixture for about 10 seconds, pouring the mixture in a tray used in Example 2, and irradiating light.

Experimental Example: Evaluation of Physical Properties of Superabsorbent Polymer The physical properties of the base polymers and the superabsorbent polymers prepared according to the above examples and comparative examples were evaluated by the following methods.

(1) Centrifuge Retention Capacity (CRC)

The centrifuge retention capacity (CRC) for a physiological saline solution was measured for the base polymers and the superabsorbent polymers in accordance with the EDANA recommended test method No. WSP 241.2.

Specifically, $W_0(g)$ (about 0.2 g) of the polymers were uniformly put in a nonwoven fabric-made bag, followed by sealing. Then, the bag was immersed in a physiological saline solution composed of a 0.9 wt % aqueous sodium chloride solution (physiological saline solution) at room temperature. After 30 minutes, water was removed from the bag by centrifugation at 250 G for 3 minutes, and the weight $W_2(g)$ of the bag was then measured. Meanwhile, the same procedure was carried out without using an empty bag not including the polymers, and then the resultant weight $W_1(g)$ was measured.

Using the respective weights thus obtained, the centrifuge retention capacity was determined according to the following Calculation Equation 1.

$$CRC(g/g) = \{[W_2(g) - W_1(g)]/W_0(g)\} - 1 \quad \text{[Calculation Equation 1]}$$

In the above calculation equation 1, $W_0(g)$ is an initial weight (g) of the superabsorbent polymer, $W_1(g)$ is a weight of the empty bag not including the superabsorbent polymer, which is measured after dehydrating the superabsorbent polymer by using a centrifuge at 250 G for 3 minutes, and $W_2(g)$ is a weight of the bag including the superabsorbent polymer, which is measured after immersing and absorbing the superabsorbent polymer in a physiological saline solution at room temperature for 30 minutes and then dehydrating the same by using a centrifuge at 250 G for 3 minutes.

(2) Absorption Rate (Vortex Time) of Superabsorbent Polymer

The vortex time of the base polymer and the superabsorbent polymer was measured in seconds according to the method described in International Publication WO 1987/003208.

Specifically, the vortex time was calculated by measuring the amount of time required for the vortex to disappear after adding 2 grams of the polymers to 50 mL of physiological saline solution (0.9 wt sodium hydroxide aqueous solution) in seconds, and then stirring the mixture at 600 rpm. At this time, a stirring bar of 31.8×8 mm available from Bel-Art Products Inc. was used.

(3) Absorbency Under Load (AUL)

The absorbency under load (AUL) for a physiological saline solution was measured for the superabsorbent polymers in accordance with the EDANA recommended test method No. WSP 242.2.

Specifically, a 400 mesh stainless screen was installed in the bottom of a plastic cylinder having an inner diameter of 25 mm. $W_0(g)$ (about 0.16 g) of a superabsorbent polymer for measuring the absorbency under load was uniformly scattered on the screen under conditions of room temperature and relative humidity of 50%. Then, a piston which could uniformly provide a load of 6.3 kPa (0.9 psi) was put thereon. At this time, the piston used was designed so that the outer diameter was slightly smaller than 25 mm and thus it could move freely up and down without any significant gap with the inner wall of the cylinder. Then, the weight $W_3(g)$ of the device prepared in this way was measured.

After putting a glass filter having a diameter of 90 mm and a thickness of 5 mm in a Petri dish having a diameter of 150 mm, a 0.90 wt % sodium hydroxide aqueous solution (physiological saline solution) was poured in the Petri dish. At this time, the physiological saline solution was poured until the surface level became equal to the upper surface of the glass filter. Then, a sheet of filter paper having a diameter of 90 mm was put on the glass filter.

Subsequently, the prepared device was placed on the filter paper so that the superabsorbent polymer in the device was swelled by the physiological saline solution under load. After one hour, the weight $W_4(g)$ of the device containing the swollen superabsorbent polymer was measured.

Using the weight thus measured, the absorbency under load was calculated according to the following Calculation Equation 2.

$$AUL(g/g) = [W_4(g) - W_3(g)] / W_0(g) \quad \text{[Calculation Equation 2]}$$

in the above calculation equation 2, $W_0(g)$ is an initial weight (g) of the superabsorbent polymer, $W_3(g)$ is the total sum of a weight of the superabsorbent polymer and a weight of the device capable of providing a load to the superabsorbent polymer, $W_4(g)$ is the total sum of the weight of the superabsorbent polymer and a weight of the device capable of providing a load to the superabsorbent polymer, after absorbing a physiological saline solution in the superabsorbent polymer under a load (about 0.9 psi) for 1 hour.

TABLE 1

| | Mixing time[a] [s] | Foam stabilizer | Base polymer | | Surface-crosslinked superabsorbent polymer | | |
|---|---|---|---|---|---|---|---|
| | | | CRC [g/g] | vortex time[b] [s] | CRC [g/g] | vortex time[c] [s] | 0.9 AUL [g/g] |
| Example 1 | 0 | Not used | 39.0 | 50 | 31.8 | 39 | 18.1 |
| Comparative Example 1 | 20 | Not used | 40.8 | 59 | 32.4 | 50 | 17.2 |
| Comparative Example 2 | 60 | Not used | 40.4 | 84 | 32.6 | 72 | 16.9 |
| Example 2 | 0 | Used | 36.4 | 47 | 31.3 | 34 | 20.2 |
| Example 3 | 5 | Used | 36.1 | 48 | 31.0 | 38 | 20.2 |
| Comparative Example 3 | 10 | Used | 37.1 | 50 | 30.9 | 41 | 20.9 |
| Example 4 | 5 | Used | 37.3 | 47 | 30.8 | 38 | 19.6 |

[a] As a mixing time after addition of the foaming agent, it is defined as the time between the contact of the neutralized acrylic acid with the foaming agent and the light irradiation.
[b] Absorption time measured by using a polymer (base polymer or superabsorbent polymer) having a particle diameter of 300 to 600 μm which was passed through a U.S. standard 30 mesh screen and retained on a U.S. standard 50 mesh screen.
[c] Absorption time measured by using a superabsorbent polymer having a particle diameter of 90 to 850 μm which was passed through a U.S. standard 20 mesh screen and retained on a U.S. standard 170 mesh screen.

The invention claimed is:

1. A method for preparing a superabsorbent polymer comprising:
   irradiating light within 9 seconds from the moment when a water-soluble ethylenically unsaturated monomer having at least partially neutralized acidic groups makes contact with a foaming agent, and performing crosslinking polymerization via light irradiation of a monomer mixture containing the water-soluble ethylenically unsaturated monomer having at least partially neutralized acidic groups, and the foaming agent, in the presence of an internal crosslinking agent to prepare a hydrogel polymer;
   drying, pulverizing, and classifying the hydrogel polymer to form a base polymer powder; and
   additionally crosslinking a surface of the base polymer powder in the presence of a surface crosslinking agent to form a surface-crosslinked layer,
   wherein the superabsorbent polymer has a centrifuge retention capacity (CRC) for a physiological saline solution of 29 to 33 g/g and absorbency under load (AUL) of under 0.9 psi for a physiological saline solution of 14 to 22 g/g, and a vortex time of 20 to 40 seconds.

2. The method for preparing a superabsorbent polymer of claim 1, wherein the monomer mixture further contains, as a foam stabilizer, an alkyl sulfate salt, an alkyl sulfonate salt, an alkyl phosphate salt, an alkyl carbonate salt, a polyethylene glycol alkyl ester, a polypropylene glycol alkyl ester, a glucoside alkyl ester, a glycerol alkyl ester, a block-copolymer of polyethylene glycol and polypropylene glycol, or a mixture thereof.

3. The method for preparing a superabsorbent polymer of claim 1, wherein in the preparing a hydrogel polymer, the foaming agent is added to the monomer mixture in a solid or liquid state without dilution, the foaming agent is added in a solution state after being diluted in a solvent and, the foaming agent is added by spraying, or the forming agent is added by spraying it on a coating film obtained by coating the monomer mixture.

4. The method for preparing a superabsorbent polymer of claim 1, wherein the foaming agent is at least one carbonate selected from the group consisting of sodium hydrogencarbonate, sodium carbonate, potassium hydrogencarbonate, and potassium carbonate.

5. The method for preparing a superabsorbent polymer of claim 1, wherein the foaming agent is added in an amount of 0.001 to 1% by weight based on the total amount of the monomer mixture.

6. The method for preparing a superabsorbent polymer of claim 1, wherein the irradiating light is performed within 5 seconds from the moment when the water-soluble ethylenically unsaturated monomer having at least partially neutralized acidic groups makes contact with the foaming agent.

7. The method for preparing a superabsorbent polymer of claim 1, wherein the internal crosslinking agent is at least one selected from the group consisting of polyethylene glycol diacrylate, glycerin diacrylate, glycerin triacrylate, unmodified or ethoxylated trimethylolpropane triacrylate, hexanediol diacrylate, and triethylene glycol diacrylate.

8. The method for preparing a superabsorbent polymer of claim 1, wherein the surface crosslinking agent is at least one polyol selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, and glycerol, or at least one carbonate compound selected from the group consisting of ethylene carbonate and propylene carbonate.

* * * * *